US005299338A

United States Patent [19]

Foster

[11] Patent Number: 5,299,338

[45] Date of Patent: Apr. 5, 1994

[54] HOSPITAL BED WITH PIVOTING HEADBOARD

[75] Inventor: L. Dale Foster, Brookville, Ind.

[73] Assignee: Hill-Rom Company, Inc., Batesville, Ind.

[21] Appl. No.: 65,880

[22] Filed: May 21, 1993

Related U.S. Application Data

[60] Division of Ser. No. 33,958, Mar. 19, 1993, which is a continuation of Ser. No. 525,044, May 18, 1990, which is a division of Ser. No. 309,886, Feb. 14, 1989, Pat. No. 5,072,906, which is a continuation-in-part of Ser. No. 144,188, Jan. 15, 1988, Pat. No. 4,811,435.

[51] Int. Cl.[5] ...................... A61B 19/02; F16M 13/00

[52] U.S. Cl. ........................................ 5/658; 248/122; 248/282; 312/209

[58] Field of Search ............. 5/658, 600, 503.1, 507.1; 248/122, 124, 125, 282, 283, 289, 323, 324, 325.1, 326, 327; 312/209

[56] References Cited

U.S. PATENT DOCUMENTS 2,694,439 11/1954 Murray ............................ 248/282
3,627,250 12/1971 Pegram .
4,345,847 8/1982 Schff et al. .
4,452,499 6/1984 Verburg ............................ 312/209
4,500,134 2/1985 Kaneko .
4,607,897 8/1986 Schwartz .
4,673,154 6/1987 Karapita .
4,714,222 12/1987 Kiesel et al. .
4,783,036 11/1988 Vossoughi .
4,795,122 1/1989 Petre .
4,801,815 6/1989 Biette .
4,856,741 8/1989 Schaefer .
4,934,933 6/1990 Fuchs .................................. 312/209
4,993,683 2/1991 Kreuzer .

FOREIGN PATENT DOCUMENTS 1534200 11/1978 United Kingdom .

OTHER PUBLICATIONS

Kreuzer, INCAREport . . ., the focus is on the patient Friedhelm Kreuzer GmbH.
Drager, "The Ideal Intensive Care Unit" ICU 9000; Dragerwerk AG Lubeck, Fed. Rep. of Germany.

*Primary Examiner*—Flemming Saether
*Attorney, Agent, or Firm*—Wood, Herron & Evans

[57] ABSTRACT

In a hospital room, arms are pivoted on vertical axes that pass through the head and foot ends of a patient's bed. One of the arms carries a computer terminal at its free end. The other arm carries a power column or a portion of a power column at its free end. The arms are swingable around the end of the bed and to either side of the bed, whereupon the person attending the patient can use the instruments on the arms at the point of care for the patient.

3 Claims, 4 Drawing Sheets

HOSPITAL BED WITH PIVOTING HEADBOARD

This application is a divisional of prior application Ser. No. 08/033,958, filed Mar. 19, 1993, now pending, which is a continuation of Ser. No. 07/525,044, filed May 18, 1990, pending, which is a divisional of Ser. No. 07/309,886, filed Feb. 14, 1989, now U.S. Pat. No. 5,072,906, which is a continuation in part of Ser. No. 07/144,188 filed Jan. 15, 1988, now U.S. Pat. No. 4,811,435.

BACKGROUND OF THE INVENTION

This invention relates to the location of patient care instruments with respect to a patient's bed.

A modern critical-care room has a computer terminal and display. The nurse or other person attending the patient uses the computer terminal to bring up the person's chart electronically, to determine what procedures have been prescribed for the care of the patient, can administer those procedures to the patient, can take vital signs and can make appropriate entries in the computer of the patient's condition and the care that has been given the patient, thereby bringing the patient's chart up-to-date.

The computer terminal is usually on a stand in the patient's room, the terminal being accessible but nevertheless out of the way of the attendant's movements as the attendant administers to the patient. The attendant may make two, three or four trips to the terminal in a brief (up to ten minutes) visit to the patient's room.

Similarly, the patient's room has been provided with a headwall or power column. The headwall or power column presents electrical outlets for patient care equipment, gas and vacuum outlets and many accessories for the care of the patient, including an infusion pump, a sphygmomanometer and cuff for taking blood pressure, drainage equipment and a monitor for the display of regular or continuously-monitored patient data, including EKG data, blood pressure data and the like. The headwall and power column have been fixed, usually at or close to the wall of the patient's room adjacent the head end of the patient's bed. In some instances, in the case of a headwall, some items of equipment are duplicated on each side of the patient's bed so as to be available to the patient on either side of the bed, depending upon the patient's condition. In instances where it is necessary to administer a code procedure to the patient having heart arrest, the bed itself must be moved away from the headwall or power column in order to make available the head end of the bed for access to the patient.

BRIEF DESCRIPTION OF THE INVENTION

An objective of the present invention has been to provide patient care instruments such as the computer terminal and the power column in a position that is immediately accessible at the point of patient care and is out of the way of the movement of persons attending the patient in both the routine nursing care and emergency procedures.

This objective of the invention is attained by mounting the patient care instruments on arms that swing about pivot axes passing through either or both ends of the patient's bed. The pivotal mounting permits the swinging of the instruments to any position on an arc that passes from one side of the bed across the end of the bed to the other side of the bed. To appreciate the advantage of the invention, consider the computer terminal in relation to the nurse making a routine nursing call upon a patient. The nurse enters the patient's room and proceeds to the side of the patient's bed at the "point of care." The point of care is the position at which the nurse can check the patient's vital signs, check the IV administration, check any drainage system, and observe the monitor.

The nurse swings the computer terminal to the point of care. Without taking steps to operate the computer terminal, the nurse can bring the patient's chart upon the terminal screen and can perform all the nursing tasks required. All of the data concerning the patient's care and condition is entered while the nurse stands at the point of care.

The advantage of a swinging power column is similar to that of the swinging computer terminal. The instruments on the power column are brought both to the side of the patient where they are most conveniently used in the patient's care. That position of the power column would normally be immediately adjacent the selected point of care. Thus, with the swinging power column, the walking required by the nurse in attending the patient is reduced to an absolute minimum in that no steps should be required for the use of the instrumentation on the power column and no steps should be required for the use of the computer terminal.

In addition to "steps saved," the swinging power column adds space flexibility for optimumally positioning a ventilator, IV pumps, eliminating lines crossing over crossing over the patient and otherwise keeping "points of care" free of obstructing equipment. Further, the flexible power column positioning allows the column to fit the type of patient being cared for, neurosurgery, heart surgery, etc.

The pivoting power column feature of the invention admits of a variation wherein the power column can be fixed but the power column has a pivotably nesting section, the nesting section containing the instrumentation that is conveniently brought to the patient's side. On the upper and fixed part of the column would be the monitor which normally can be viewed from any point of care. As a further modification, however, it is contemplated that the monitor screen be mounted on a frame that is rotatable in the power column so that the monitor can be positioned for viewing from either side of the bed. It is known to mount the monitor on an arm projecting from a known power column. In accordance with the present invention, the monitor would be positioned in vertical alignment with the power column so as to minimize the lateral space required by the combination of power column and monitor.

The invention contemplates a power column and/or computer used with a hospital bed of the type wherein the bed is very mobile and the patient never leaves the bed as he is moved from point to point, such as surgery, X-ray, therapy and the like. To this end, the invention provides a swinging power column or computer terminal mounted on an arm which is pivoted to the hospital room floor. At the pivot point, the apparatus may have a docking connection, that is, a receptacle into which the bed moves to connect the bed to the normal power equipment employed in raising and lowering the bed and adjusting the position of the patient. With this embodiment, when the mobile bed is rolled into position, the axis of the pivoting arm will pass through the end, normally the head end, of the bed.

The invention further contemplates the docking connection having, in addition to electrical and power signals, a source of hospital air to control the inflation of sleeping surfaces that may be mounted on hospital beds.

Since the apparatus of the present invention will be in place whether or not a bed is at its normal position, reference will be made hereinafter to a bed site, it being understood that the bed site is a rectangular area on which the bed is positioned when the bed and patient are in the critical-care room.

BRIEF DESCRIPTION OF THE DRAWINGS

The several features and objectives of the present invention will become more readily apparent from the following detailed description taken in conjunction with the accompanying drawings in which.

DETAILED DESCRIPTION OF THE DRAWINGS

Figure 1:
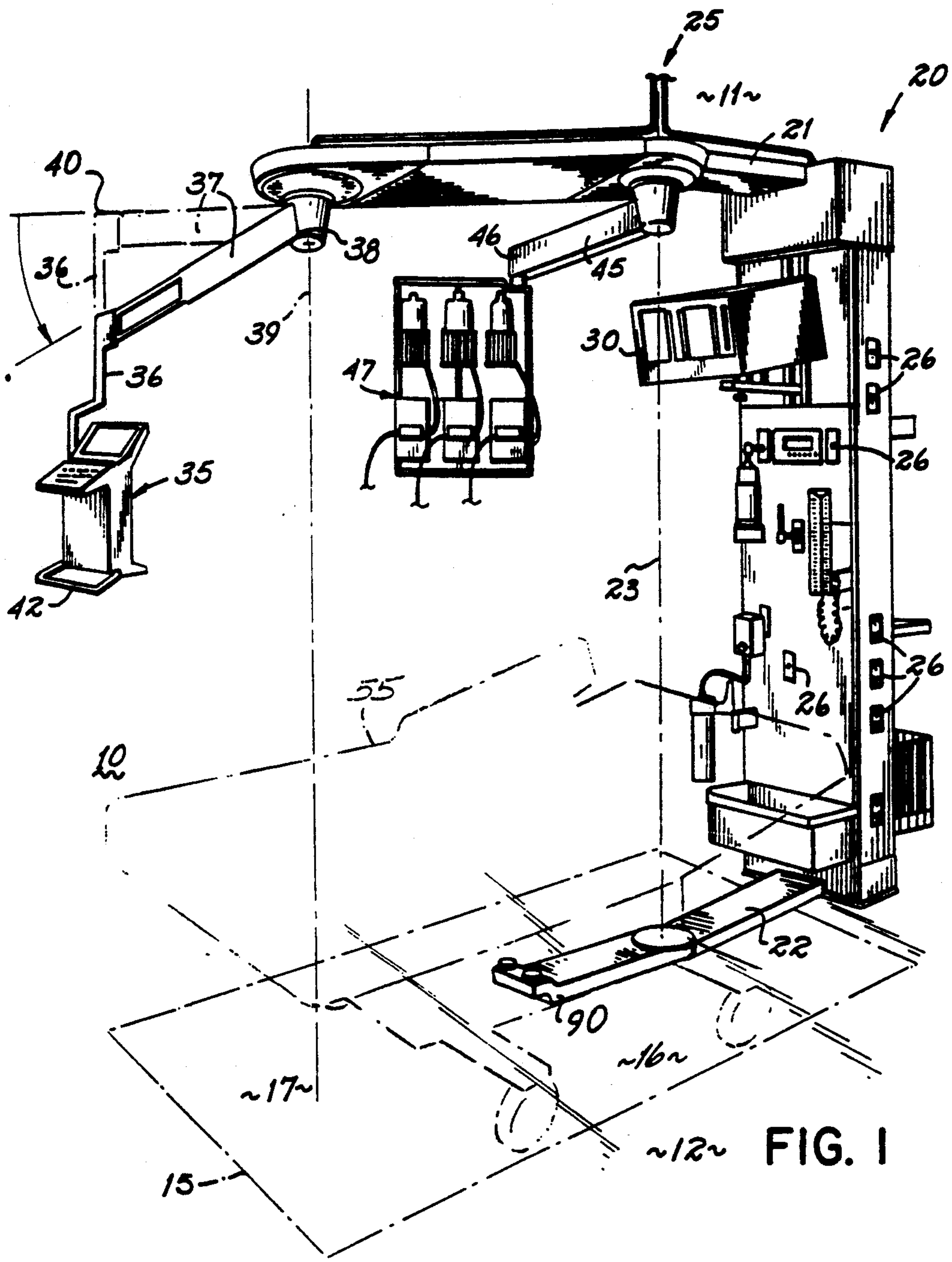
FIG. 1 is a diagrammatic perspective view of apparatus in accordance with the present invention.

Referring particularly to FIG. 1, a hospital room 10 has a ceiling 11, a floor 12, and the usual walls, not shown. A rectangular bed site 15 is shown in phantom lines on the floor 12. The bed site has a head end 16 and a foot end 17. The position of the head end and foot end, of course, can be reversed. A power column 20 is mounted at its upper end on a swinging arm 21 and at its lower end to a swinging arm 22. The arms 21 and 22 are pivoted on an axis 23 which passes through the head end 16 of the bed site 15 and coincides with the longitudinal centerline of the bed site. The arm 21 is pivoted to the ceiling 11 and the arm 22 is pivoted to the floor 12. At the ceiling, electrical and gas conduit 25 pass from the ceiling through the arm 21 to the power column 20. Those conduit 25 are terminated at electrical, gas and vacuum outlets 26 as are conventional in power columns and headwalls. A monitor 30 is mounted in the upper portion of the power column 20, the monitor providing real time, continuous wave forms depicting the patient's heart condition, blood pressure, etc. It is contemplated that the power column have the capability of swinging through an arc of approximately 120° and be infinitely positionable at any point along the arc. The arc extends from one side of the bed through the end of the bed to the other side of the bed.

At the opposite end of the bed, a computer terminal 35 is suspended by a bracket 36 from an arm 37. The arm has an end 38 that is pivoted to the ceiling 11 about an axis 39 passing through the foot end of the bed. The mounting for the arm preferably has a counterweight or counterspring which permits the arm to be easily raised to the phantom line position 40 in FIG. 1 or lowered to the full line position as shown. The computer terminal preferably has a handle 42 to assist the attending in moving the terminal up and down as well as in a horizontal arcuate direction.

The pivot connection for the arm 37 permits the terminal to be swung through an arc of at least 180° so as to bring the terminal to an infinite number of positions through an arc passing from one side of the bed through the foot end of the bed to the other side of the bed.

The invention further contemplates the option of providing a pivoting pump rack arm 45 having one end pivoted on the axis 23 of the power column and having a free end 46 that supports a pump rack 47. The pump rack contains different types of administration sets and infusion pumps for administering intraveneously to the patient. The pivoting arm 45 makes the pump rack accessible to either side of the bed. The pump rack 45 is mounted on the center line of the patient and swings in a 180° arc (opposite the power column rotation) over the patient.

Figure 2:
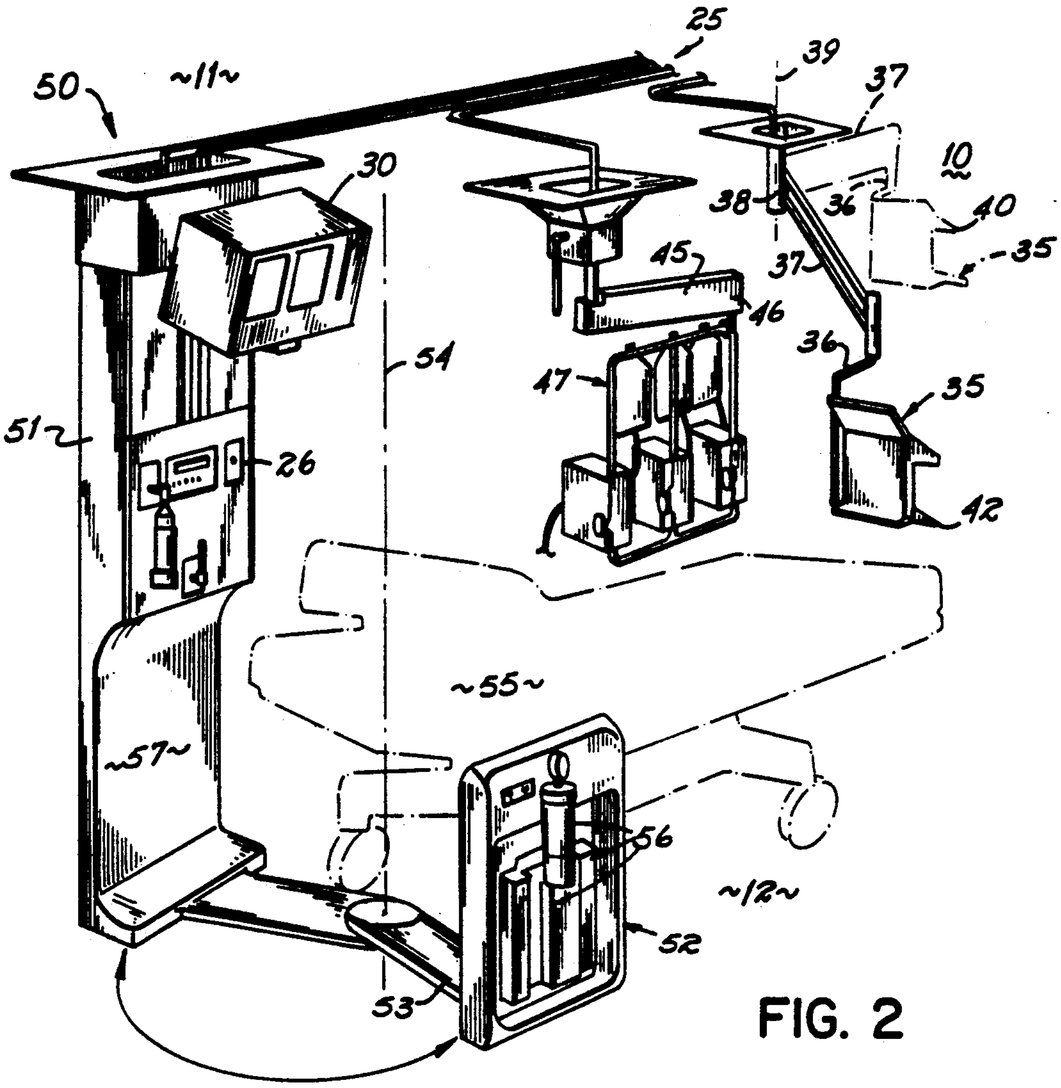
FIG. 2 is a diagrammatic, disassembled perspective view of an alternative form of the invention.

A modification of the power column is shown in FIG. 2. In accordance with FIG. 2, a power column 50 has a fixed section 51 and a pivotal section 52. The pivotal section may contain oxygen, vacuum and accessories 56 for the treatment of the patient. It is preferably mounted on an arm 53 that is pivoted on an axis 54 passing through the head end of a bed 55. The fixed section 51 has a recess 57 into which the pivotal section can be swung when it is not in use. In this embodiment of the invention, it is preferred that the fixed section 51 be mounted at the corner of the bed site so as to leave the head end of the bed 55 available for code procedures. The pivot section 52 has an available path of movement of about 120°, as does the power column 20 of FIG. 1.

Among the advantages of the pivotal section of a fixed power column is that it makes medical gases available simultaneously on both sides of the patient with gases available from the columns as well as the pivoting section. The pivoting section can also carry a small ventilator or a tram, a tram being a device for carrying small vital signs equipment.

Figure 3:
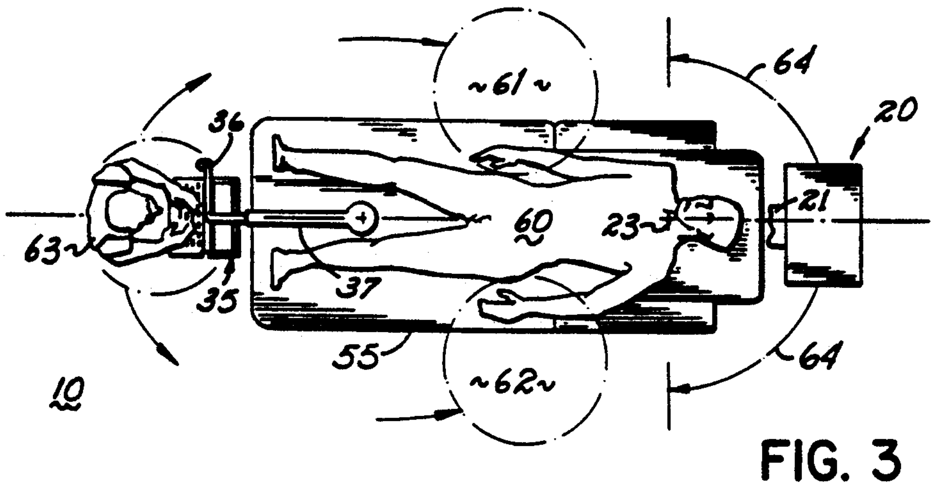
FIG. 3 is a diagrammatic plan view illustrating the operation of the invention.

The diagrammatic illustration of FIG. 3 shows the manner in which the invention operates. A bed 55 has a patient 60. On either side of the bed are points of care 61 and 62. The computer terminal 35 operated by a nurse or other attendant 63 can be positioned adjacent either of the points of care whereby to permit the nurse to perform all of the administrative functions with a minimum of movement about the patient's room 10. Similarly, the power column 20 is movable about the path 64 to either side of the bed as well as to the head of the bed 55. In the code procedure, if necessary, the power column 20 is movable completely out of the way of the persons attending the patient.

Figure 4:
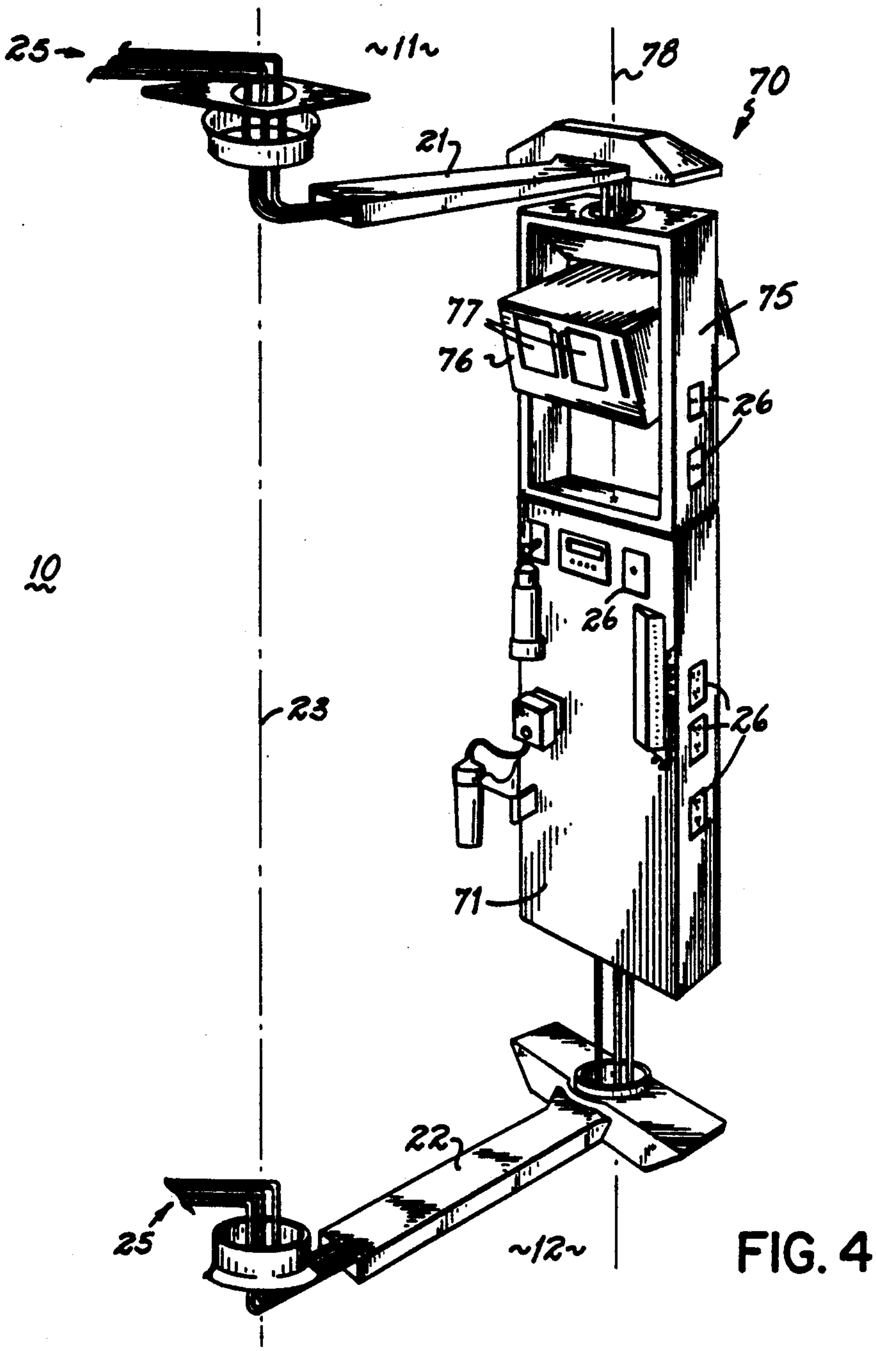
FIG. 4 is a diagrammatic, disassembled perspective view of an alternative embodiment of a power column in accordance with the present invention.

In still another modification of the invention, shown in FIG. 4 a power column 70 is pivoted on upper and lower arms 21 and 22. The power column has a lower section 71 which is fixed to the arm 22. The upper section is a rectangular frame 75 which is pivoted to the arm 21 and to the lower section 71 on the axis 23. Within the frame 75 is a monitor 76. The monitor 76 is pivoted for movement about a horizontal axis within the frame 75. The frame 75 is pivoted about a vertical axis 78. With movement about both axes, the monitor screen 77 is conveniently visible to the nurse from any position that the nurse assumes next to the patient. Furthermore, the monitor itself is tucked within the frame rather than projecting from the power column as is conventional with existing columns, thereby conserving space around the patient.

Figure 5:
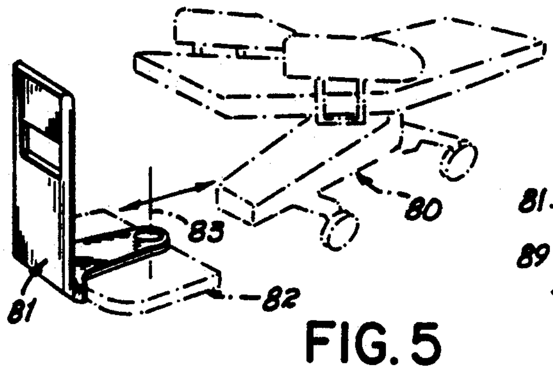
FIG. 5 is a perspective view of an alternative form of the invention.
Figure 6:
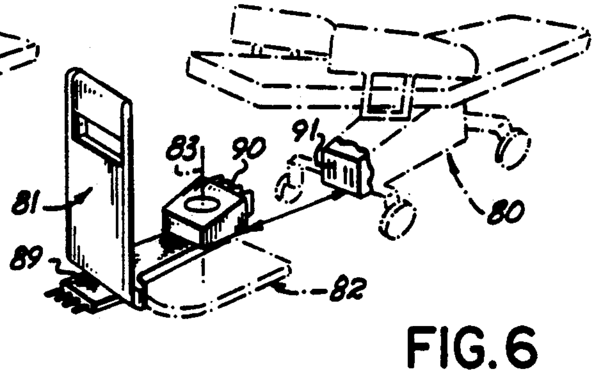
FIG. 6 is a perspective view of the modification of the alternative form of the invention of FIG. 5.

In the embodiment of FIG. 5, a bed 80 has a headboard/control center 81 associated with it. The headboard/control center is mounted on a pedestal 82 for pivoting about an axis 83. This headboard is electrically self-contained and does not have controls that are connected to the bed to operate it. While it may contain a computer, the computer is electrically self-contained. In the embodiment of FIG. 6, a connector unit or dock 90 is mounted on the pedestal 82 and contains electrical connections to all of the controls on the headboard-/control center 81. A tail 89 projecting rearward from the pedestal contains all of the connections to be made to the hospital circuits—the power, nurse call, phone and computer power supply. A mating connector 91 is mounted on the bed 80. When the bed and pedestal are brought together to locate the headboard at one end of the bed, the electrical connection to all four systems is made by plugging the connector 90 into the connector 91. This modification may thus be provided with all of the controls for operating the bed and the like. Power to the computer from the hospital circuits remains connected even though the bed is pulled away.

Figure 7:
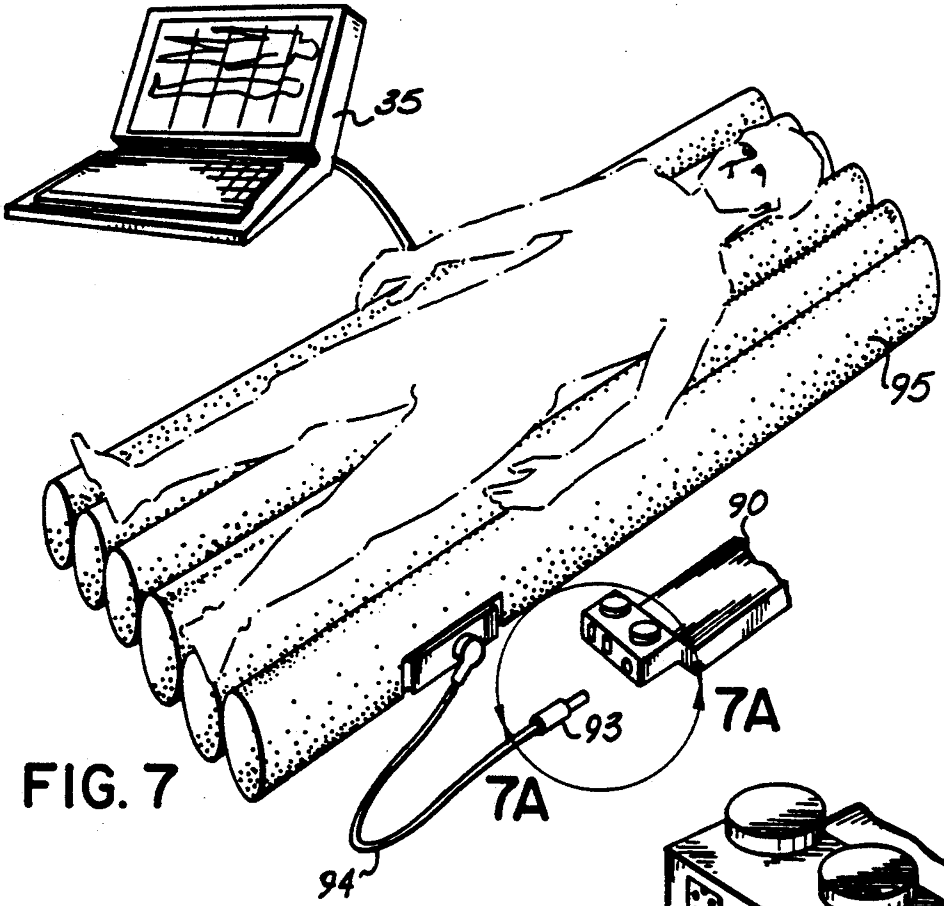
FIG. 7 is a fragmentary perspective view of a modification of FIG. 6.
Figure 7A:
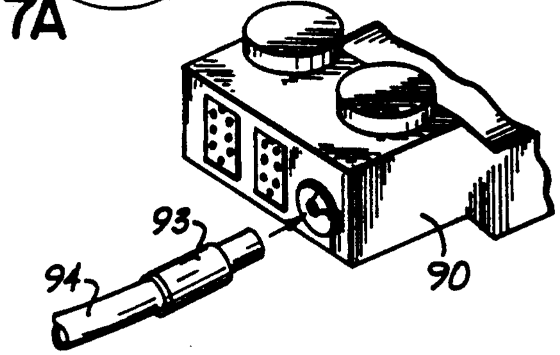
FIG. 7A is an enlarged view of the area within the circle of FIG. 7.

As shown in FIG. 7, the fixed dock 90 to which the mobile bed is connected can also be provided with an air outlet 93 connected via a hose 94 to a computerized air mattress 95. A similar provision could be made to the dock 90 of FIG. 1. It is contemplated that the program pressure mapping for the mattress would be a part of the program of the computer 35 at the work center. With control by the computer, air would inflate and deflate the patient support surface to the pressure tailored for the patient and his specific condition.

Preferably, in both embodiments the headboard is pivotally mounted so that in the normal day-by-day routine, the headboard can be swung to the side of the bed to permit the nurse to perform the routine tasks associated with a patient visit. In code situations, however, the bed and headboard/control center are quickly separated to leave the space at the end of the bed totally unobstructed during the code situation procedures.

The terms "control center" or "work center" are deemed to generically embrace the computer terminal as well as the power column.

From the above disclosure of the general principles of the present invention and the preceding detailed description of a preferred embodiment, those skilled int he art will readily comprehend the various modifications to which the present invention is susceptible. Therefore, I desire to be limited only by the scope of the following claims and equivalents thereof:

I claim:

1. Apparatus for a hospital room having a floor comprising:

an elongated, generally rectangular hospital bed having a head end and a foot end, a power column having electrical outlets, gas outlets, a monitor for the display of patient data, and other patient-treating accessories, said power column being mounted adjacent said bed, an arm having one end pivotally mounted on said floor on an axis which is under the head end of the bed, the other end of said arm being connected to a patient care section forming a part of said power column to permit said patient care section to swing through an arc that passes from one side of said bed past the end of said bed to the other side of said bed.

2. Apparatus as in claim 1 in which said power column is fixed at one corner of said bed site, said arm swinging through an arc of about 120°.

3. Apparatus as in claim 1 in which said power column has a recess, a fixed arm projecting from a point on said power column adjacent said recess and having an end, close to the room floor underlying said bed, said pivotally mounted arm being pivoted to one end of said fixed arm.

* * * * *